(12) United States Patent
Collet et al.

(10) Patent No.: US 9,617,566 B2
(45) Date of Patent: Apr. 11, 2017

(54) CONTROL OF BIOREACTOR PROCESSES

(71) Applicant: LanzaTech New Zealand Limited, Auckland (NZ)

(72) Inventors: Christophe Collet, Auckland (NZ); Guy William Waters, Auckland (NZ); Jason Carl Bromley, Auckland (NZ); Justin Yi Yang, Auckland (NZ); Jarod Nathan Wilson, Auckland (NZ)

(73) Assignee: LANZATECH NEW ZEALAND LIMITED, Auckland (NZ)

( * ) Notice: Subject to any disclaimer, the term of this patent is extended or adjusted under 35 U.S.C. 154(b) by 0 days.

(21) Appl. No.: 14/329,881

(22) Filed: Jul. 11, 2014

(65) Prior Publication Data
US 2016/0010116 A1   Jan. 14, 2016

(51) Int. Cl.
   *C12P 7/06*       (2006.01)
(52) U.S. Cl.
   CPC .............. *C12P 7/065* (2013.01); *Y02E 50/17* (2013.01)
(58) Field of Classification Search
   None
   See application file for complete search history.

(56) References Cited

U.S. PATENT DOCUMENTS

| | | | |
|---|---|---|---|
| 5,173,429 A | 12/1992 | Gaddy et al. | |
| 5,593,886 A | 1/1997 | Gaddy | |
| 6,368,819 B1 | 4/2002 | Gaddy et al. | |
| 8,383,376 B2 | 2/2013 | Simpson et al. | |
| 8,975,013 B2 | 3/2015 | Snyder | |
| 2011/0212433 A1 | 9/2011 | Barker et al. | |
| 2012/0258441 A1* | 10/2012 | Gebauer et al. | 435/3 |
| 2013/0045517 A1 | 2/2013 | Oakley et al. | |
| 2013/0130339 A1 | 5/2013 | Hermann et al. | |

(Continued)

FOREIGN PATENT DOCUMENTS

| | | |
|---|---|---|
| EP | 1117309 EP | 9/1984 |
| WO | WO98/00558 | 1/1998 |

(Continued)

OTHER PUBLICATIONS

D Herbert, R Elsworth, RC Telling. The Continuous Culture of Bacteria: a Theoretical and Experimental Study. J Gen Microbiol 1956, vol. 14, p. 601-622.*

(Continued)

*Primary Examiner* — John S Brusca
*Assistant Examiner* — Olivia Wise
(74) *Attorney, Agent, or Firm* — Frank S Molinaro (57) ABSTRACT

Processes, as well as associated systems and computer program (software) products, are disclosed for the biological conversion of CO into desired end products such as ethanol. The control methodologies used for these processes can advantageously result in a reduced time required for a batch operation or other initial operating period, prior to achieving a continuous operation, which may be demarcated either by the addition of fresh culture medium at a defined flow rate or by another process initiation target. The control methodologies may alternatively, or in combination, improve a process performance parameter, such as productivity of the desired end product or bacterial growth rate, during this batch operation or other initial operating period.

10 Claims, 7 Drawing Sheets

(56) References Cited

U.S. PATENT DOCUMENTS

| | | |
|---|---|---|
| 2013/0203143 A1 | 8/2013 | Schultz et al. |
| 2013/0210096 A1 | 8/2013 | Schultz et al. |
| 2013/0316411 A1 | 11/2013 | Schultz |
| 2014/0142352 A1 | 5/2014 | Dauner et al. |

FOREIGN PATENT DOCUMENTS

| | | |
|---|---|---|
| WO | WO00/68407 | 1/2000 |
| WO | WO02/08438 | 1/2002 |
| WO | WO2007/117157 | 10/2007 |
| WO | WO2008/115080 | 9/2008 |
| WO | WO2009/022925 | 2/2009 |
| WO | WO2010/093262 | 8/2010 |
| WO | WO2011/002318 | 1/2011 |

OTHER PUBLICATIONS

Oshiro, Mugihito et al., Efficient conversion of lactic acid to butanol with pH-stat continuous lactic acid and glucose feeding method by Clostridium saccharoperbutylacetonicum, Applied Microbiology and Biotechnology, 2010, vol. 87, No. 3, pp. 1177-1185.

International Search Report for International Patent Application PCT/US2015/029563, Korean Intellectual Property Office, Jul. 27, 2015.

Abrini et al., (1994), *Clostridium autoethanolgenum*, sp. Nov., an anaerobic bacterium that produces ethanol from carbon monoxide. Archives of Microbiology 161: 345-351.

\* cited by examiner

CONTROL OF BIOREACTOR PROCESSES

FIELD OF THE INVENTION

Aspects of the invention relate to the initiation of processes for the microbial fermentation of CO-containing substrates to ethanol, for example to achieve continuous and steady-state operation. Specific aspects relate to the manner in which operating parameters are controlled, leading to advantageous results.

DESCRIPTION OF RELATED ART

Environmental concerns over fossil fuel greenhouse gas (GHG) emissions have led to an increasing emphasis on renewable energy sources. As a result, ethanol is rapidly becoming a major hydrogen-rich liquid transport fuel around the world. Continued growth in the global market for the fuel ethanol industry is expected for the foreseeable future, based on increased emphasis in ethanol production in Europe, Japan, and the United States, as well as several developing nations. For example, in the United States, ethanol is used to produce E10, a 10% mixture of ethanol in gasoline. In E10 blends, the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. In addition, the European Union (EU) has mandated targets, for each of its member nations, for the consumption of sustainable transport fuels such as biomass-derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value in the marketplace for competing uses, namely as food sources for both humans and animals. In addition, the cultivation of starch or sucrose-producing crops for ethanol production is not economically sustainable in all geographies, as this is a function of both local land values and climate. For these reasons, it is of particular interest to develop technologies to convert lower cost and/or more abundant carbon resources into fuel ethanol. In this regard, carbon monoxide (CO) is a major, energy-rich by-product of the incomplete combustion of organic materials such as coal, oil, and oil-derived products. CO-rich waste gases result from a variety of industrial processes. For example, the steel industry in Australia is reported to produce and release into the atmosphere over 500,000 metric tons of CO annually.

More recently, micro-organism (bacterial) based process alternatives for producing ethanol from CO on an industrial scale have become a subject of commercial interest and investment. The ability of micro-organism cultures to grow, with CO being the sole carbon source, was first discovered in 1903. This characteristic was later determined to reside in an organism's use of the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic, and acetogenic organisms have since been shown to metabolize CO. Anaerobic bacteria, such as those from the genus *Clostridium*, are known to produce ethanol from CO, $CO_2$ and $H_2$ via the acetyl CoA biochemical pathway. For example, various strains of *Clostridium ljungdahlii* that produce ethanol from gases are described in WO 00/68407; EP 1117309 A1; U.S. Pat. No. 5,173,429; U.S. Pat. No. 5,593,886; U.S. Pat. No. 6,368,819; WO 98/00558; and WO 02/08438. The bacterium *Clostridium* autoethanogenum sp is also known to produce ethanol from gases (Abrini et al., ARCHIVES OF MICROBIOLOGY 161: 345-351 (1994)).

Because each enzyme of an organism promotes its designated biological conversion with essentially perfect selectivity, microbial synthesis routes can achieve higher yields with lower energy costs compared to conventional catalytic routes. For example, the energy requirements for separating byproducts, which result from non-selective side reactions, from the desired products may be reduced. In addition, concerns over the poisoning of catalysts, due to impurities in the reaction medium, are diminished.

Despite these apparent advantages, however, the art must address certain challenges associated with microbial synthesis of ethanol from CO, especially in terms of ensuring that the production rate is competitive with other technologies. When using CO as their carbon source, the anaerobic bacteria described above produce ethanol by fermentation, but they also produce at least one metabolite, for example $CO_2$, $H_2$, methane, n-butanol, and/or acetic acid. The formation of any of these metabolites has the potential to significantly impact productivity and overall economic viability of a given process, as available carbon is lost to the metabolite(s) and the production efficiency of the desired end product is compromised. In addition, unless a metabolite (e.g., acetic acid) itself has value at the time and place of the microbial fermentation process, it may pose a waste disposal problem. Various proposals for addressing the formation of products other than the desired end product in the anaerobic fermentation of CO-containing gases to make ethanol are discussed in WO2007/117157, WO2008/115080 and WO2009/022925.

Ethanol production rate, which is a key determinant as to whether a given fermentation process is economically attractive, is highly dependent on managing the appropriate conditions for bacterial growth. For example, it is known from WO2010/093262 that the CO-containing substrate must be provided to a microbial culture at a rate that results in optimal microbial growth and/or desired metabolite production. If insufficient substrate is provided, microbial growth slows and the fermentation product yields shift toward acetic acid at the expense of ethanol. If excessive substrate is provided, poor microbial growth and/or cell death can result. Further information regarding the relationships among operating parameters in these processes is found in WO2011/002318.

The control of operating parameters is particularly important during the initial period of operation, in which the processing objectives are focused on not only growing the cell culture to a sufficient level and establishing other conditions for continuous operation, but also balancing the product and byproduct productivities. Reducing the time needed for conducting a batch culture operation, prior to continuous bioreactor operation, has major implications for improving process economics. This is particularly true in view of the fact that microbes capable of growing on CO-containing gases generally do so at a slower rate than microbes used in competing technologies with sugars as a food source. From the commercial perspective of operating a fermentation process, the time required for a microbial population to become established, i.e., to reach a sufficiently high cell density for the synthesis of economically favorable levels of product, represents a key operating cost affecting the overall profitability. The ability to enhance culture growth rates and/or productivities during an initial operating period, for example under batch conditions, and thereby reduce the time required to reach desired cell densities and/or product levels, is an important determinant for overall success in the commercialization of biological processes for producing ethanol from CO-containing waste gas.

SUMMARY OF THE INVENTION

Aspects of the invention relate to methods for controlling the initiation of biological CO conversion processes, based on available data. Normally, at the beginning of such processes, the bioreactor is charged (inoculated) with a culture medium containing carboxydotrophic bacteria (i.e., having the ability to derive energy from CO). According to representative processes, ethanol is the desired end product, whereas acetate is generated as an undesired metabolite, in the form of acetic acid. As discussed above, CO must be supplied judiciously to the bioreactor to meet competing objectives. In particular, an undersupply of CO can result in excessive acetate formation at the expense of ethanol, whereas an oversupply of CO can negatively impact bacterial growth. In view of these considerations, a specified profile for the flow rate over time of CO or CO-containing gas may be used, based on the expected bacterial growth during batch operation, in conjunction with information derived from other processes.

The overriding operating objective during an initial operating period (e.g., a batch operation period) is to increase the concentration of bacteria (biomass), in the culture medium. Therefore, the gas flow profile during the batch operation period is normally conservative and seeks to avoid the oversupply of CO. This can result in the formation of acetic acid in a significant amount, in some cases exceeding that of the desired ethanol end product. Because any acetic acid that is generated throughout the bacterial conversion processes lowers the pH value of the culture medium, a basic neutralizing agent such as aqueous ammonium hydroxide may be introduced. The neutralizing agent may be dosed to the bioreactor to maintain a pH value (e.g., a pH of 5.0) of the culture medium suitable for bacterial growth.

Embodiments of the invention are directed to biological fermentation processes for converting CO into a desired end product such as ethanol, comprising feeding both a CO-containing substrate and a basic neutralizing agent (e.g., aqueous ammonium hydroxide) to a bioreactor comprising a culture medium containing carboxydotrophic bacteria. The processes generate both the desired end product as well as an acidic metabolite (e.g., acetic acid) that is converted by the neutralizing agent (e.g., to a salt such as ammonium acetate), in order to avoid unacceptable pH levels in the culture medium. According to one representative embodiment, the flow rate of the basic neutralizing agent may be controlled based on a measured property, such as a measured concentration or measured productivity of the carboxydotrophic bacteria or acidic metabolite, in the culture medium. Alternatively, if such measured property is unavailable, for example, if suitable on-line sampling and analytical equipment are lacking, the flow rate of the basic neutralizing agent may be controlled based on a measured flow rate of the CO-containing substrate or otherwise based on a set point for this substrate.

Other embodiments of the invention are directed to systems comprising a bioreactor and a controller configured to control the flow rate of the basic neutralizing agent to the bioreactor, based on either a measured property of the culture medium as described above or, alternatively, based on a measured flow rate of the CO-containing substrate or otherwise based on a set point for this substrate. In the case of control based on a measured property of the culture medium, the system may further comprise the necessary sampling apparatus, configured to isolate a sample of the culture medium from the bioreactor for analysis, in addition to an analyzer configured to analyze the isolated sample. In either of the above control method alternatives, representative systems may optionally comprise a second controller configured to control a CO-containing substrate flow rate based on a measured pH value, a sampling apparatus configured to isolate, from the bioreactor, a sample of the culture medium, and/or an analyzer configured to analyze the sample and then input, to the controller, the measured pH value.

Further embodiments of the invention are directed to computer program products comprising non-transitory computer readable media having computer programs embodied thereon. These computer programs include instructions for causing a processor to perform steps needed to carry out the control processes described herein. These processes include receiving information that is input to a controller configured to control a basic neutralizing flow rate to a bioreactor. The information that may be received and input, in this manner, includes information received from an analyzer configured to analyze a culture medium sample from the bioreactor for a measured property as described above. Alternatively, the information may be the measured flow rate of the CO-containing substrate, received from a flow rate sensor or measurement device that is configured to measure this flow. The received information may also include a CO-containing substrate flow rate set point. Regardless of the type of information that is received and input to a controller, representative processes may further comprise receiving a measured pH value, for example, from a pH meter or other analyzer configured to measure the pH of the culture medium directly or otherwise a sample of the culture medium from the bioreactor. The measured pH value may be input to a second controller configured to control the CO-containing substrate flow rate, whereby the measured pH value is the basis for control.

These and other embodiments and aspects relating to the present invention are apparent from the following Detailed Description.

BRIEF DESCRIPTION OF THE DRAWINGS

A more complete understanding of the exemplary embodiments of the present invention and the advantages thereof may be acquired by referring to the following description in consideration of the accompanying figures.

DETAILED DESCRIPTION

The present invention relates to processes for producing a desired end product, such as ethanol, by feeding CO in a CO-containing substrate to a bioreactor comprising a culture medium containing carboxydotrophic bacteria. In addition to the desired end product, representative processes additionally generate undesired or less desired metabolites. An example of an acidic metabolite that may be generated in addition to a desired product, such as ethanol, is acetate (e.g., in the form of acetic acid). Representative carboxydotrophic bacteria or microbes (i.e., microorganisms that obtain energy and carbon from CO), are those from the genus *Moorella, Clostridia, Ruminococcus, Acetobacterium, Eubacterium, Butyribacterium, Oxobacter, Methanosarcina, Methanosarcina*, and *Desulfotomaculum*. Particular examples of bacteria that are Clostridia include *C. ljundahlii, C. autoethanogenum, C. ragsdalei*, and *C. beijerenckei*.

Representative CO-containing substrates include broadly any CO-containing gas, or possibly liquid, in which carbon monoxide can be made available to one or more strains of bacteria for growth and/or fermentation. Such CO-containing substrates preferably do not include contaminants to the extent that such contaminants might have an adverse effect on the growth of the carboxydotrophic bacteria (e.g., one or more contaminant(s) are not present in concentrations or amounts such that the growth rate is reduced by more than 10% under a given set of conditions, compared to the growth rate under the same conditions, but without the contaminant (s)). Representative gaseous CO-containing substrates typically contain a significant proportion of CO, preferably at least about 5% to about 100% CO by volume. Such substrates are often produced as waste products of industrial processes such as steel manufacturing processes or non-ferrous product manufacturing process. Other processes in which gaseous CO-containing substrates are generated include the gasification of organic matter such as methane, ethane, propane, coal, natural gas, crude oil, low value residues from oil refinery (including petroleum coke or petcoke), solid municipal waste or biomass. Biomass includes by-products obtained during the extraction and processing of foodstuffs, such as sugar from sugarcane, or starch from maize or grains, or non-food biomass waste generated by the forestry industry. Any of these carbonaceous materials can be gasified, i.e. partially combusted with oxygen, to produce synthesis gas (syngas comprising significant amounts of $H_2$ and CO). Advantageously, gas streams from these processes may be used as described herein for the beneficial production of useful end products such as ethanol. In other embodiments, the substrate comprising CO can be derived from the steam reforming of hydrocarbons. These processes are described in more detail in US Application publication Nos. US2013/0045517A1; US2013/0210096A1; US2013/0203143A1 and US2013/0316411A1 and U.S. Pat. No. 8,383,376 the contents of all of which are incorporated by reference in their entirety.

While it is not necessary for the CO-containing substrate to contain any hydrogen, the presence of $H_2$ is normally not detrimental to the formation of the desired end product. In particular embodiments, the CO-containing substrate may comprise low concentrations of Hz, for example, less than 10% by volume, less than 5% by volume, or less than 1% by volume. The CO-containing substrate may also contain some $CO_2$, for example, from about 1% to about 80% by volume, from about 1% to about 50% by volume, or from 1% to about 30% by volume. Any CO-containing substrate, such as a gaseous CO-containing substrate, may be treated to remove any undesired impurities, such as dust particles or any other solid, liquid, or gaseous contaminants that may be detrimental to the carboxydotrophic bacteria or the biological conversion process in general, prior to its use in the biological conversion process. For example, the gaseous CO-containing substrate may be filtered or scrubbed using known methods.

In the context of an acidic metabolite that is acetic acid, the terms "acetic acid" or "acetate" refer to the total acetate present in the culture medium, either in its anionic (dissociated) form (i.e., as acetate ion or $CH_3COO^-$) or in the form of free, molecular acetic acid ($CH_3COOH$), with the ratio these forms being dependent upon the pH of the system. The term "bioreactor" includes any suitable vessel for containing a culture of carboxydotrophic bacteria that may be used to carry out the biological processes described herein, which may also be referred to as fermentation processes, to the extent that they are generally conducted anaerobically. A suitable bioreactor may be a Continuous Stirred Tank Reactor (CSTR), an Immobilized Cell Reactor (ICR), a Trickle Bed Reactor (TBR), a Moving Bed Biofilm Reactor (MBBR), a Bubble Column, a Gas Lift Fermenter, a Membrane Reactor such as Hollow Fiber Membrane Bioreactor (HFMBR), a Static Mixer, or may include other vessels or devices (e.g., towers or piping arrangements) suitable for contacting the CO-containing substrate with the bacterial culture medium (e.g., with dissolution and mass transport kinetics favorable for carrying out the biological conversion).

Other suitable process streams, operating parameters, and equipment for use in the biological processes described herein are described in U.S. patent application Publication No. US2011/0212433, which is hereby incorporated by reference in its entirety.

The present invention is more particularly associated with the discovery of biological processes for converting CO to valuable end products such as ethanol, in which (i) the time required for a batch operation period or other initial operating period, prior to achieving a continuous operation, which may be demarcated either by the addition of fresh culture medium at a defined flow rate or by another process initiation target, is unexpectedly reduced and/or (ii) productivity of the desired end product or another process performance parameter (e.g., bacterial growth rate) is unexpectedly improved during this batch operation period or other initial operating period. The conversion from batch operation to continuous operation may be demarcated by the commencement of adding fresh culture medium to the bioreactor used in the process. Alternatively, if the rate of fresh culture medium addition is increased gradually rather than commenced at a discreet time point, the conversion from batch to continuous operation may be demarcated by achieving a target rate of fresh culture medium addition to, and/or achieving a target rate of bacteria-containing culture medium withdrawal from, the bioreactor. The target rates of fresh culture medium addition and/or bacteria-containing culture medium withdrawal may be the rates associated with a steady-state operation, i.e., an operation under which conditions are held substantially constant over an extended period (e.g., at least about 3 days, or at least about 10 days) of production of a desired end product. Otherwise, these target rates may be at least about 60%, at least about 75%, or at least about 90% of the rates associated with steady-state operation.

Aside from a target rate of fresh culture medium, other process initiation targets that may be used to demarcate an initial operating period from a steady-state or "on-stream" operating period can include a culture medium concentration of desired product (e.g., ethanol), carboxydotrophic bacteria, or acidic metabolite. Process initiation targets may also include a productivity of desired product, carboxydotrophic bacteria, or acidic metabolite. Process initiation targets may be predetermined, i.e., established from the outset of the process and possibly used as inputs to control systems, including computer program (software) products, used for monitoring and/or control of the biological processes, including monitoring and/or control of the addition of fresh culture medium.

Particular embodiments of the invention are based on the finding that certain control methodologies, which may be automated, can effectively match the flow rate of the CO-containing substrate to a measured property of the culture medium. These methodologies, when used in an initial operating period (e.g., a batch operation period), or when used in general, advantageously provide a significantly improved balance in terms of the reduction in acetic acid or acetate production, coupled with the avoidance of oversupplying CO. Surprisingly, objectives of the batch operation period or other initial operating period can be achieved much sooner and also much more efficiently in terms of productivities of both the desired end product and undesired metabolite(s), compared to the conventional practice of establishing a CO-containing gas flow rate profile from the outset. According to some embodiments, overall process economics may be greatly improved as a result of the reduced startup time for achieving a bacteria concentration in the culture medium that allows for transition to continuous operation. For example, the time from inoculation of the bioreactor until a given biomass bacteria concentration is achieved may be reduced by at least about 20% (e.g., from about 20% to about 80%), typically by at least about 35% (e.g., from about 35% to about 75%), and often by at least about 50% (e.g., from about 50% to about 70%), compared to results achieved using conventional practices for controlling process parameters.

According to one particular control methodology, a property of the culture medium, measured during an initial operating period (e.g., a batch operation period) or during some other operation period (e.g., a continuous, steady-state, or normal operation period), is used as the basis for control of the flow rate of a basic neutralizing agent (e.g., aqueous ammonium hydroxide). Representative properties include a concentration of an acidic metabolite (e.g., acetic acid or acetate), a productivity of an acidic metabolite, a concentration of the carboxydotrophic bacteria, a productivity of the carboxydotrophic bacteria, or a combination of such properties. In general, an increase in any of these properties will directionally lead to an increase in the flow rate of the basic neutralizing agent. In one specific embodiment, the basic neutralizing agent flow rate is controlled based on a targeted acidic metabolite concentration in the culture medium, which is in turn determined from a measured concentration of the carboxydotrophic bacteria. In this manner, the control methodology accounts for the consumption of the basic neutralizing agent, and specifically the increased utilization of nitrogen, by the growing bacterial culture. This advantageously provides conditions during startup (e.g., a batch operation period) that are specifically tailored to the objectives of rapidly growing the bacterial culture with a favorable product yield distribution.

The property of the cell culture medium may be measured continuously or intermittently, for example periodically, with the period of time between each successive measurement being generally from every 0.1 seconds to every 120 seconds, typically from every 0.5 seconds to every 60 seconds, and often from every second to every 10 seconds. The measured property may be obtained by on-line analysis of the concentration, in the culture medium, of either the carboxydotrophic bacteria or the acidic metabolite. Based on successive measurements of concentration (e.g., in grams per liter, g/l), together with the time interval between successive measurements, the productivities (e.g., in grams per liter per day, $g/l \cdot day^{-1}$) of the carboxydotrophic bacteria or the acidic metabolite can be calculated. For example if the concentration of carboxydotrophic bacteria is determined at successive intervals, designated Time 1 and Time 2, then the productivity of the carboxydotrophic bacteria at Time 2 may be expressed as follows: (concentration at Time 2−concentration at Time 1)/(Time 2−Time 1).

Generally, the acidic metabolite concentration is measured in a culture medium sample that is free or substantially free of carboxydotrophic bacteria, as a result of filtration or membrane separation. For example, a filter having a suitable pore size (e.g., in the range of 0.05 μm to 1 μm) for removing the bacteria may be incorporated on a sample line of a sampling system configured to withdraw cell-free culture medium from a single reactor, or otherwise configured to withdraw such liquid from multiple reactors (e.g., from 2 to 10 reactors, such as 4 to 6 reactors, which may operate in series or parallel, or otherwise operate independently) at different times, in order to automatically and separately monitor the performance of the reactors. According to other embodiments, a cell-free sample of the culture medium may be available as a permeate stream from a membrane separation system, in which the cell-rich retentate stream is recycled to the bioreactor. The permeate, if not used for analysis, may normally flow to a second bioreactor (e.g., operating in series). Cell-free filtrate or permeate obtained from the bioreactor can provide representative samples used for the on-line measurement of the properties of end product (e.g., ethanol) concentration or acidic metabolite (e.g., acetic acid or acetate) concentration. These concentrations may be determined by known analytical methods, such as chromatography (e.g., high pressure liquid chromatography, or HPLC).

In the case of carboxydotrophic bacteria concentration as the measured property, the culture medium may be withdrawn directly from the bioreactor, for example as a bleed stream that may normally flow to a second bioreactor (e.g., operating in series) if not used for analysis. A sample line from a bleed stream or other stream for withdrawing cell culture medium may be fluidly connected to a suitable analytical device for the on-line measurement of the property of carboxydotrophic bacteria concentration. Representative devices include those measuring the absorbance or transmission of electromagnetic energy through the sample (e.g., a spectrophotometer), a certain biological activity of the sample (e.g., a plate reader), or another property of the sample (e.g., impedance/capacitance) in a disposable or reusable probe (e.g., an on-line biomass probe). The sample line from a bleed stream or other stream may be part of a sampling system configured to withdraw culture medium from a single reactor, or otherwise configured to withdraw such liquid from multiple reactors (e.g., from 2 to 10 reactors, such as 4 to 6 reactors, which may operate in series or parallel, or otherwise operate independently) at different times, in order to automatically and separately monitor the performance of the reactors.

Sampling systems for the on-line analysis of culture media from one or multiple bioreactors will include suitable conduits (e.g., tubing or piping) valves, pumps, and actuators to allow the automated sampling of a desired reactor at a desired time, and suitable devices for flushing (purging) sample lines to obtain accurate results. In the case of analyzing the cell-free culture medium, for example to obtain the concentration of ethanol or acetate, filtered liquid or membrane permeate, as described above, may be fed (e.g., pumped using a peristaltic pump) at least intermittently, but preferably continuously, through a suitable sample container that is configured for on-line analysis. For example, inlet and outlet lines in fluid communication with such a sample container (e.g., a sample vial) may continuously lead a filtered stream of culture medium to and from the sample container. The continuous feed of culture medium through a sample container, according to some embodiments, will involve flowing a cell-free permeate or filtrate stream, as described above, from the sample container inlet, through the sample container, and to the sample container outlet over some period of operation of the bioreactor, for example over at least about 3 minutes, at least about 5 minutes, or at least about 10 minutes. According to a specific embodiment, for example, filtered, cell-free culture medium may be fed continuously through the sample container for 9 minutes, followed by a 1 minute backflush of the filter on the sample line, in order to prevent filter plugging. Excess culture medium that is not sampled and that flows through the sample container outlet, may be discarded as waste.

In this manner, the liquid present in the sample container is representative of the cell-containing culture medium in the bioreactor, in terms of the concentrations of the desired end product (e.g., ethanol) and metabolite(s) (e.g., acetic acid or acetate) in this cell-containing culture medium at the time of analysis of the cell-free culture medium in the sample container. The lengths of the sample lines may be minimized to minimize any offset between the actual concentration(s) of end product and/or metabolite(s) in the bioreactor and the measured concentration(s) of the cell-free culture medium in the sample container at the time of analysis. According to some embodiments, the offset between the actual and measured concentration of the end product and/or a metabolite will be less than about 10%, less than about 5%, or less than about 2%. A sample of the cell-free culture medium may therefore be withdrawn from the sample container and analyzed, in order to determine the concentration(s) of end product and metabolite(s) in the bioreactor essentially in real time. For example, automated sampling may involve using a sampling needle to pierce a rubber seal on the top of the sample container and withdraw a sample of cell-free culture medium at regular intervals, with a period of time between successive measurements being as described above. An automated sampling apparatus may include, for example, from 2 to 10 sample containers, such as 4 to 6 sample containers, for sampling culture media from the same number of bioreactors, which may operate in series or parallel, or otherwise operate independently.

More generally, automated sampling apparatuses may be configured, using suitable conduits (e.g., tubing or piping) valves, pumps, and actuators, for analysis of both the cell culture medium and cell-free culture medium, as described above, of multiple reactors (e.g., from 2 to 10 reactors, such as 4 to 6 reactors, which may operate in series or parallel, or otherwise operate independently) at different times, in order to automatically and separately monitor the performance of the reactors. Properties of the culture medium, including the concentration and productivity of metabolite(s) (e.g., acetic acid or acetate) and/or the concentration and productivity of the carboxydotrophic bacteria, may be determined automatically at regular intervals, with a period of time between successive measurements being as described above. Advantageously, the use of on-line, automated sampling and analysis allows the analytical results to be directly input to the relevant controller (e.g., for controlling the flow rate of the basic neutralizing agent), without human intervention. In addition, automated sampling apparatuses as described herein allow for the monitoring of properties of a bioreactor culture medium, or multiple bioreactor culture media, on an essentially real-time basis, without the need for operators to track and handle, for example by performing dilutions and/or pipetting, multiple liquid samples from multiple bioreactors. Reliability and data reproducibility are thereby significantly improved, as well as the overall operation of the bioreactor(s).

Preferably, the control methodologies as described herein are automated, involving the use of a computer program with appropriate instructions for causing a processor to transmit the necessary signals to controllers for carrying out these control methodologies. According to a particular control methodology, a measured property of the culture medium is used as the basis for controlling the flow rate of the basic neutralizing agent (e.g., a hydroxide compound, such as aqueous ammonium hydroxide or other inorganic or organic base). Such a control methodology can, compared to conventional control methodologies, advantageously reduce the time of an initial operating period (e.g., a batch operation period), for example prior to a period of steady-state or continuous operation, which may be demarcated by a defined rate of withdrawal of a desired end product (e.g., ethanol) or other defined operating parameter. Without being bound by theory, the reduction in time may be attributed at least partly to the fact that the carboxydotrophic bacteria utilize or consume the basic neutralizing agent (e.g., utilize nitrogen in the basic neutralizing agent). In general, therefore, control methodologies as described herein are particularly advantageous in bioreactor processes in which at least two feed streams (e.g., both a CO-containing substrate and a basic neutralizing agent) to the culture medium are consumed, metabolized, or otherwise utilized by the bacteria contained therein. In other embodiments, control methodologies described herein may be used for both a batch operation period and a continuous operation period, or for a continuous operation period only.

Representative properties include a measured concentration (i.e., in units of mass/volume, such as grams/liter or grams·liter$^{-1}$) or a measured productivity (i.e., in units of mass/(volume·time), such as grams/(liter·day) or grams·liter$^{-1}$·day$^{-1}$) of the acidic metabolite (e.g., acetic acid or acetate), or of the carboxydotrophic bacteria. According to preferred embodiments, the measured property is a measured concentration or measured productivity of the acidic metabolite. Any of the above properties may be measured continuously or intermittently (e.g., periodically) during an initial operating period (e.g., a batch operation period) or other period, with a measurement frequency, and using sampling techniques, as described above. For example, a sample of a permeate stream that is cell-free or at least substantially cell-free, may be analyzed for its concentration of acidic metabolite using HPLC.

Control of the flow rate of the basic neutralizing agent may, more specifically, be based on a difference between any of the measured properties of the culture medium, as described above, and their corresponding set points. For example, if an acidic metabolite measured concentration is the basis for control, then the basic neutralizing agent flow rate may be controlled based on the difference between the acidic metabolite measured concentration and an acidic metabolite set point concentration in the culture medium. Likewise, if an acidic metabolite measured productivity, a carboxydotrophic bacteria measured concentration, or a carboxydotrophic bacteria measured productivity is the basis for control, then the basic neutralizing agent flow rate may be controlled based on the difference between (i) the acidic metabolite measured productivity and an acidic metabolite set point productivity, (ii) the carboxydotrophic bacteria measured concentration and a carboxydotrophic bacteria set point concentration, or (iii) the carboxydotrophic bacteria measured productivity and a carboxydotrophic bacteria set point productivity.

In the case of an acidic metabolite set point concentration being determined, for example, if the acidic metabolite measured concentration exceeds this set point (or target) concentration, the control methodology may result in directionally decreasing the flow rate of the basic neutralizing agent. This will ultimately decrease the concentration of acidic metabolite in the culture medium, as the decreased flow rate of basic neutralizing agent will cause the pH of the culture medium to decrease. According to preferred embodiments, the CO-containing substrate flow rate may be controlled based on a measured pH value (e.g., obtained using an on-line pH meter) of the culture medium. Therefore, a decrease in the measured pH value (e.g., to below a pH value set point or target, such as 4.0, 4.5, 5.0, 5.5, or 6.0) may cause an increase in the CO-containing substrate flow rate. When the culture medium becomes supplied with an increased flow of CO-containing substrate, acidic metabolite productivity decreases in favor of ethanol productivity, causing the acidic metabolite concentration to decrease, e.g., directionally toward the acidic metabolite set point concentration, and the pH value to increase. Conversely, if the acidic metabolite measured concentration falls below the determined set point (or target) concentration, the control methodology may result in directionally increasing the flow rate of the basic neutralizing agent. This will ultimately increase the concentration of acidic metabolite in the culture medium, as the increased flow rate of basic neutralizing agent will cause the pH of the culture medium to increase.

The CO-containing substrate flow rate may be controlled based on a measured pH value (e.g., obtained using an on-line pH meter) of the culture medium, as described above. Therefore, an increase in the measured pH value (e.g., to above a pH value set point or target, such as 4.2, 4.7, 5.2, 5.7, or 6.2) may cause a decrease in the CO-containing substrate flow rate. When the culture medium becomes supplied with a decreased flow of CO-containing substrate, acidic metabolite productivity increases at the expense of ethanol productivity, causing the acidic metabolite concentration to increase, e.g., directionally toward the acidic metabolite set point concentration, and the pH value to decrease.

Figure 1:
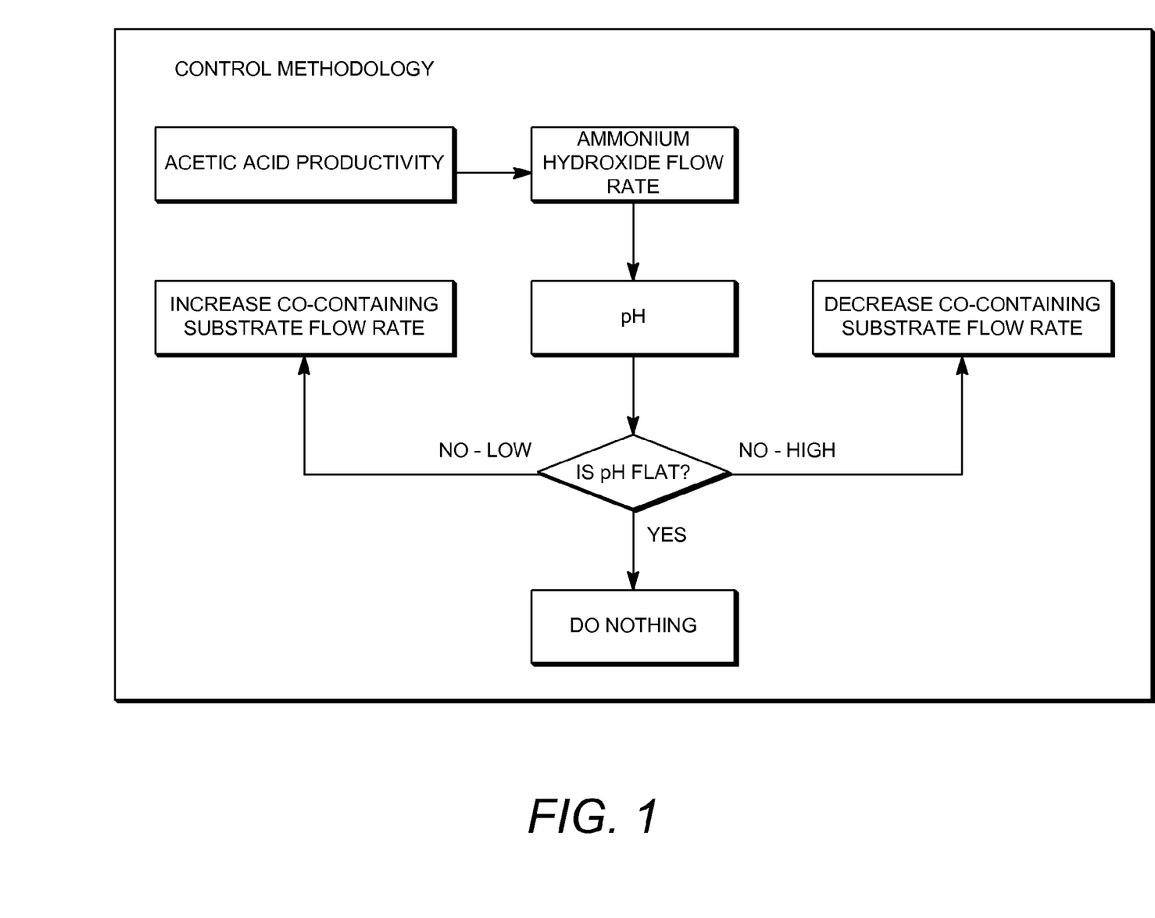
FIG. 1 is a flow chart of a representative methodology for controlling operating parameters of a biological process for converting a CO-containing substrate to ethanol.

Analogous control methodologies are possible, by controlling the flow of the basic neutralizing agent according to other measured properties of the culture medium, as described above. For example, (i) if the acidic metabolite measured productivity exceeds a corresponding set point (or target) productivity, the control methodology may result in directionally decreasing the flow rate of the basic neutralizing agent, (ii) if the carboxydotrophic bacteria measured concentration exceeds a corresponding set point (or target) concentration, the control methodology may result in directionally increasing the flow rate of the basic neutralizing agent, or (iii) if the carboxydotrophic bacteria measured productivity exceeds a corresponding set point (or target) concentration, the control methodology may result in directionally increasing the flow rate of the basic neutralizing agent. FIG. 1 depicts a representative control methodology in which the flow rate of the basic neutralizing agent, aqueous ammonium hydroxide ($NH_4OH$), is based on the measured productivity of the acidic metabolite, acetic acid. The $NH_4OH$ flow rate, in turn, affects the pH of the culture medium. If the response to any change in $NH_4OH$ flow rate is maintenance of the culture medium pH (i.e., the pH is "flat"), then the flow rate of the CO-containing substrate remains unchanged. However, if such a response increases the culture medium pH above its set point (i.e., pH is "high"), then the flow of the CO-containing substrate is decreased, increasing acetic acid productivity and bringing the pH back to its set point. If such a response decreases the culture medium pH below its set point (i.e., pH is "low"), then the flow of the CO-containing substrate is increased, decreasing the acetic acid productivity and bringing the pH back to its set point.

Any of the set points for properties of the culture medium (e.g., acidic metabolite set point concentration, acidic metabolite set point productivity, carboxydotrophic bacteria set point concentration, or carboxydotrophic bacteria set point productivity) may be determined, in turn, based on one or more other measured operating parameters (e.g., measured flow rates, concentrations, and/or productivities, or pH) of the bioreactor process. For example, the carboxydotrophic bacteria measured concentration or carboxydotrophic bacteria measured productivity may be used to determine a set point. According to a specific embodiment, and based on certain discoveries relating to the present invention, the set point may be proportional to the carboxydotrophic bacteria measured concentration or carboxydotrophic bacteria measured productivity. The acidic metabolite set point productivity, may, for example, be independently determined by the formulas $$A_1 \cdot \text{BIOCONmv} + B_1 \text{ or } A_2 \cdot \text{BIOPRODmv} + B_2$$

wherein $A_1$ and $A_2$ represent constants of proportionality between the set point and the carboxydotrophic bacteria measured concentration (BIOCONmv) or carboxydotrophic bacteria measured productivity (BIOPRODmv), respectively, and $B_1$ and $B_2$ represent offsets. The constants $A_1$ and $B_1$, or $A_2$ and $B_2$, may be determined empirically from experimental data, for example prior data obtained using the same bioreactor, or otherwise obtained using a bioreactor containing a microbial culture for carrying out the same conversion process (e.g., the conversion of CO to ethanol). More specifically, these constants may be obtained by conducting a linear regression analysis of such prior data. In the case of determining BIOCONmv or BIOPRODmv, sampling and analysis to determine the carboxydotrophic bacteria concentration may be performed as described above.

In an exemplary embodiment, therefore, a carboxydotrophic bacteria measured concentration (BIOCONmv) or carboxydotrophic bacteria measured productivity (BIOPRODmv) may be obtained using an on-line biomass probe or other sampling device and sample analyzer. From the value of BIOCONmv or BIOPRODmv, an acidic metabolite set point concentration (or target concentration) or acidic metabolite set point productivity (or target productivity) may be determined, for example according to the formulas given above.

A diluent such as fresh culture medium is generally added to the bioreactor, if not initially, then at some later point in time during the biological conversion process. The diluent may be first introduced, i.e., the diluent flow commenced, at the same time that one or more other feeds to the bioreactor (e.g., the CO-containing substrate and/or the basic neutralizing agent) are first introduced. Otherwise, the diluent may be first introduced some time after (e.g., at least about 2 hours after, at least about 6 hours after, or at least about 12 hours after) one or more other feeds to the bioreactor (e.g., the CO-containing substrate and/or the basic neutralizing agent) are first introduced. The fresh culture medium flow may be commenced after attaining a suitable culture medium commencement target, which may be the same as any of the process initiation targets as described above. Such a target may include, for example, a predetermined concentration or productivity of either the carboxydotrophic bacteria or the acidic metabolite. In general, the addition of a diluent, such as fresh culture medium, at a given mass flow rate or volumetric flow rate is accompanied (e.g., simultaneously) by the withdrawal of culture medium, including the desired end product and any metabolites, at a comparable mass flow rate or volumetric flow rate. The withdrawn culture medium may (i) be free or substantially free of carboxydotrophic bacteria (e.g., in the case of being separated by filtration or membrane separation), or (ii) contain carboxydotrophic bacteria in the same or substantially the same concentration as in the culture medium contained in the bioreactor (e.g., in the case of being withdrawn without separation). In some cases, the withdrawn culture medium may include portions (e.g., separate streams) of both (i) and (ii). In any event, either or both of (i) and (ii) may be fed to a second bioreactor for carrying out the same biological CO to ethanol conversion process (e.g., by operating in series with the first bioreactor).

Preferably, the flow rate of the diluent is increased gradually during all or part of a batch operation period as defined herein. However, it is not required that any diluent flow be added during this period, such that diluent flow is added only during a later (e.g., continuous) operation period, or such that the introduction of diluent to the bioreactor is used to demarcate the transition from a batch operating period to a continuous operating period.

As with the basic neutralizing agent flow rate, the diluent flow rate may be controlled based on any of the measured properties of the culture medium, and using any of the control methodologies, as described above. According to particular embodiments, the diluent flow rate to the bioreactor is controlled based on the carboxydotrophic bacteria measured concentration or carboxydotrophic bacteria measured productivity in the culture medium. Based on certain discoveries relating to the present invention, a diluent flow rate set point may be determined according to an exponential function, with the measured concentration or measured productivity being the exponent. For example, the diluent flow rate set point may be determined according to one of the formulas $$C_1^{(BIOCONmv)} \text{ or } C_2^{(BIOPRODmv)}$$

wherein BIOCONmv and BIOPRODmv represent, respectively, the carboxydotrophic bacteria measured concentration and the carboxydotrophic bacteria measured productivity, respectively, and $C_1$ and $C_2$ are constants. The constants $C_1$ and $C_2$ may be determined empirically from experimental data, for example from prior data obtained using the same bioreactor, or otherwise obtained using a bioreactor containing a microbial culture for carrying out the same conversion process (e.g., the conversion of CO to ethanol). In the case of determining BIOCONmv or BIOPRODmv, sampling and analysis to determine the carboxydotrophic bacteria concentration may be performed as described above.

According to a second particular control methodology, measuring a property of the culture medium is not required. Rather, prior data may be used to establish a relationships among the variables of carboxydotrophic bacteria concentration and productivity, and the corresponding flow of CO-containing gas (or substrate) of a given composition that will provide a targeted productivity of the acidic metabolite, as well as the flow of basic neutralizing agent that will maintain the pH of the culture medium. The prior data may be obtained, for example, using the same bioreactor, or otherwise using a bioreactor containing a microbial culture for carrying out the same conversion process (e.g., the conversion of CO to ethanol). By using information from other biological CO-to-ethanol conversion processes, including carboxydotrophic bacteria concentration and productivity, in addition to the corresponding flow rate of CO-containing substrate, the flow rate of the basic neutralizing agent may be estimated for a desired acidic metabolite productivity. Furthermore, using such information, the flow rate of CO-containing substrate can be estimated to supply a given carboxydotrophic bacteria concentration and achieve the desired acidic metabolite productivity.

Specific relationships among the process variables may be based, for example, on the equations below:

$$W \cdot BIOPROD + X \cdot METPROD = NEUTFLO = Y \cdot COFLO + Z$$

wherein BIOPROD, METPROD, NEUTFLO, and COFLO represent, respectively, the carboxydotrophic bacteria productivity, the acidic metabolite productivity, the basic neutralizing agent flow rate to the bioreactor, and the CO-containing substrate flow rate to the bioreactor, and W, X, Y, and Z are constants that are determined empirically based on prior data, as described above. More specifically, these constants may be obtained by conducting a linear regression analysis of such prior data. The productivities can be measured as described above (e.g., using a spectrophotometer, plate reader, or biomass probe in the case of carboxydotrophic bacteria concentration or productivity, and/or using HPLC in the case of acidic metabolite concentration or productivity).

According to particular embodiments, therefore, during a batch operating period, or other operating period, of feeding both the CO-containing substrate and basic neutralizing agent to the bioreactor, the basic neutralizing agent flow rate is controlled based on the flow rate of the CO-containing substrate. For example, the basic neutralizing agent flow rate may be controlled based on either a measured value (i.e., a CO-containing substrate measured flow rate) or otherwise a set point value (i.e., a CO-containing substrate flow rate set point). That is, a set point for the basic neutralizing agent flow rate may be determined according to such a measured value or set point value. According to certain embodiments, as is apparent from the process variable relationships set forth above, the basic neutralizing agent flow rate set point may vary linearly with either the CO-containing substrate measured flow rate or CO-containing substrate flow rate set point. Still more specifically, the basic neutralizing agent flow rate set point may be determined according to the formulas:

$$Y\text{·COFLOmv}+Z \text{ or } Y\text{·COFLOsp}+Z$$

wherein COFLOmv and COFLOsp represent, respectively, the CO-containing substrate measured flow rate and the CO-containing substrate flow rate set point. Y and Z represent constants, namely a constant of proportionality between COFLOmv or COFLOsp and the basic neutralizing agent flow rate set point, in the case of Y, and an offset, in the case of Z.

In particular types of these control methodologies, the flow rate of the CO-containing substrate may be, in turn, controlled based on the pH value of the culture medium. For example, if the pH measured value of the culture medium falls below a pH set point (e.g., one of the specific pH values indicated above), the culture medium has become too acidic, and, in response, the CO-containing substrate flow rate is increased (e.g., by automatically increasing a percentage opening of a control valve on a CO-containing substrate inlet line) to supply more CO to the bacteria culture and reduce the productivity of acid metabolite. Conversely, if the pH measured value of the culture medium rises above this pH set point, the culture medium has become too basic, and, in response, the CO-containing substrate flow rate is decreased (e.g., by automatically decreasing a percentage opening of a control valve on a CO-containing substrate inlet line) to supply less CO to the bacteria culture and increase the productivity of acid metabolite.

Alternatively, a CO-containing flow rate set point may be determined from a measured pH value of the culture medium, with this set point representing a deviation from the CO-containing flow rate measured value. In view of these considerations, it may be possible for the measured pH value of the culture medium to generate the set points for both the flow rate of the CO-containing substrate in addition to the flow rate of the basic neutralizing agent. However, it is generally preferred that the CO-containing substrate measured flow rate, this measured flow rate (as opposed to the flow rate set point) is used to determine the set point for the basic neutralizing agent flow rate. The culture medium pH value may be measured either continuously or intermittently (e.g., periodically at regular intervals) using, for example, an on-line pH analyzer. Otherwise, this pH value may be measured manually.

EXAMPLES

The following examples are set forth as representative of the present invention. These examples are not to be construed as limiting the scope of the invention as these and other equivalent embodiments will be apparent in view of the present disclosure and appended claims.

Example 1

Figure 2:
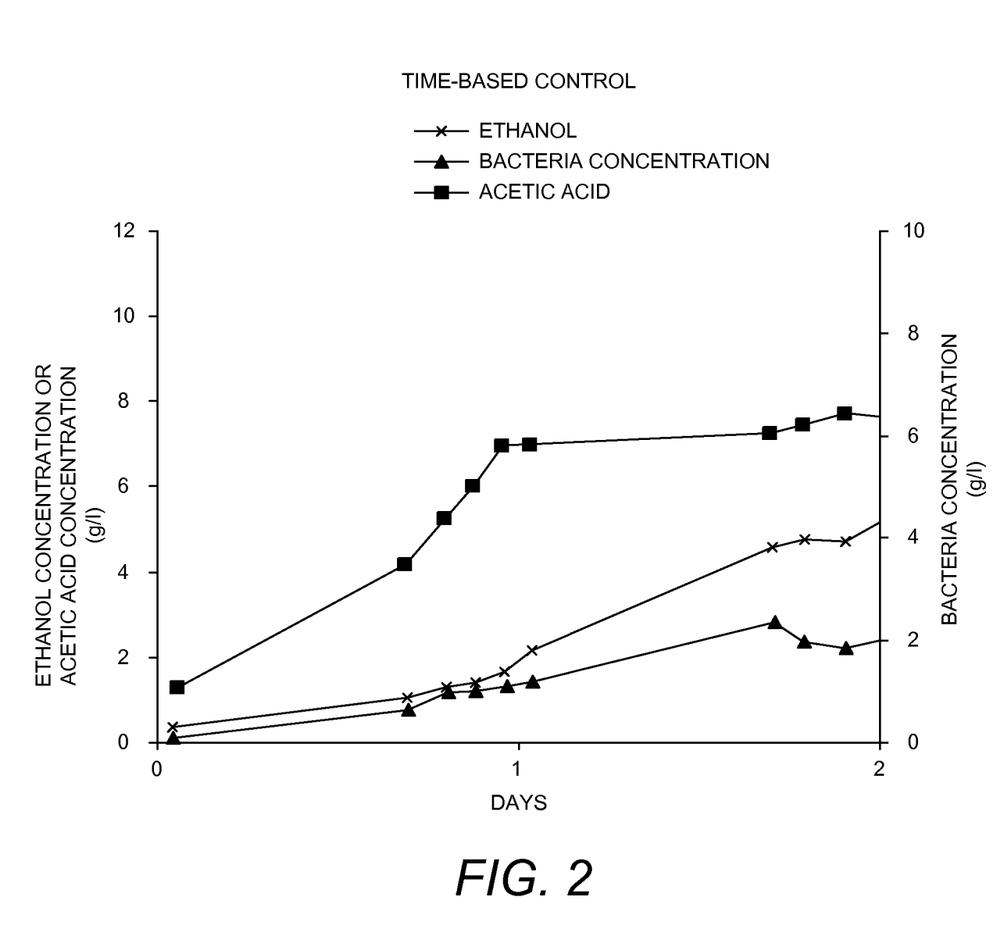
FIG. 2 is a graph of measured concentrations of ethanol, carboxydotrophic bacteria, and acetic acid, in a culture medium over time, for a biological process for converting a CO-containing substrate to ethanol, using a conventional control methodology.
Figure 3:
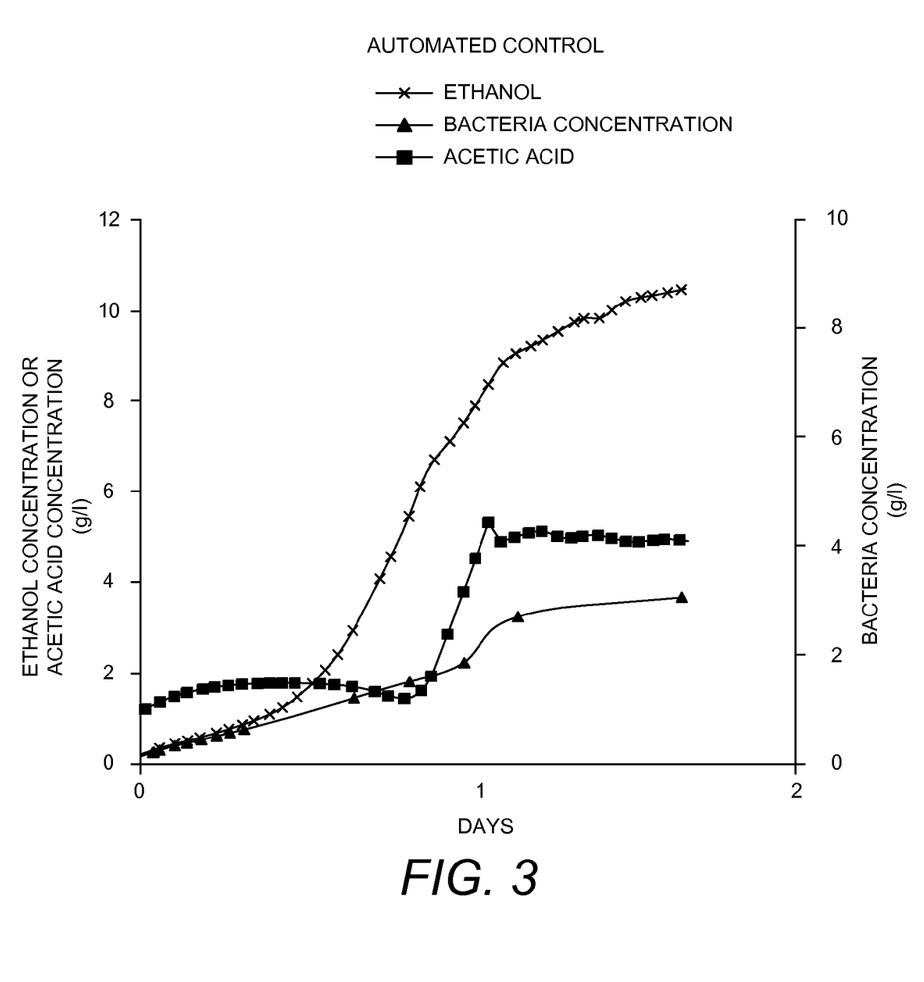
FIG. 3 is a graph of measured concentrations of ethanol, carboxydotrophic bacteria, and acetic acid in a culture medium over time, for a biological process for converting a CO-containing substrate to ethanol, using a control methodology as described herein.

Comparison of Conventional "Time-Based" Startup and Inventive "Automated" Startup A biological process for the conversion CO to ethanol was started by inoculating a bioreactor with culture medium containing C. ljundahlii. The pH of culture medium began to drop as acetic acid was produced. CO-containing substrate and ammonium hydroxide feeds to the bioreactor were started when the pH of the culture medium reached 5.0. The flow rate of the CO-containing substrate over the startup was governed by a conventional, predetermined time-based profile, in which the avoidance of CO oversupply was the main objective. For comparative purposes, the same process was started using a control methodology as described herein, in which the flow rate of the ammonium hydroxide was controlled based on the concentration of acetate (in the form of acetic acid) in the culture medium, measured automatically and periodically by HPLC. The progress of these comparative startups is shown in FIGS. 2 and 3, which provide the concentrations of ethanol, bacteria, and acetic acid in the culture medium over a period of two days. This information is provided in the case of the conventional, time-based startup (FIG. 2—"Time-Based Control") and in the case of the automated startup (FIG. 3—"Automated Control"), according to a representative embodiment of the invention.

Figure 4:
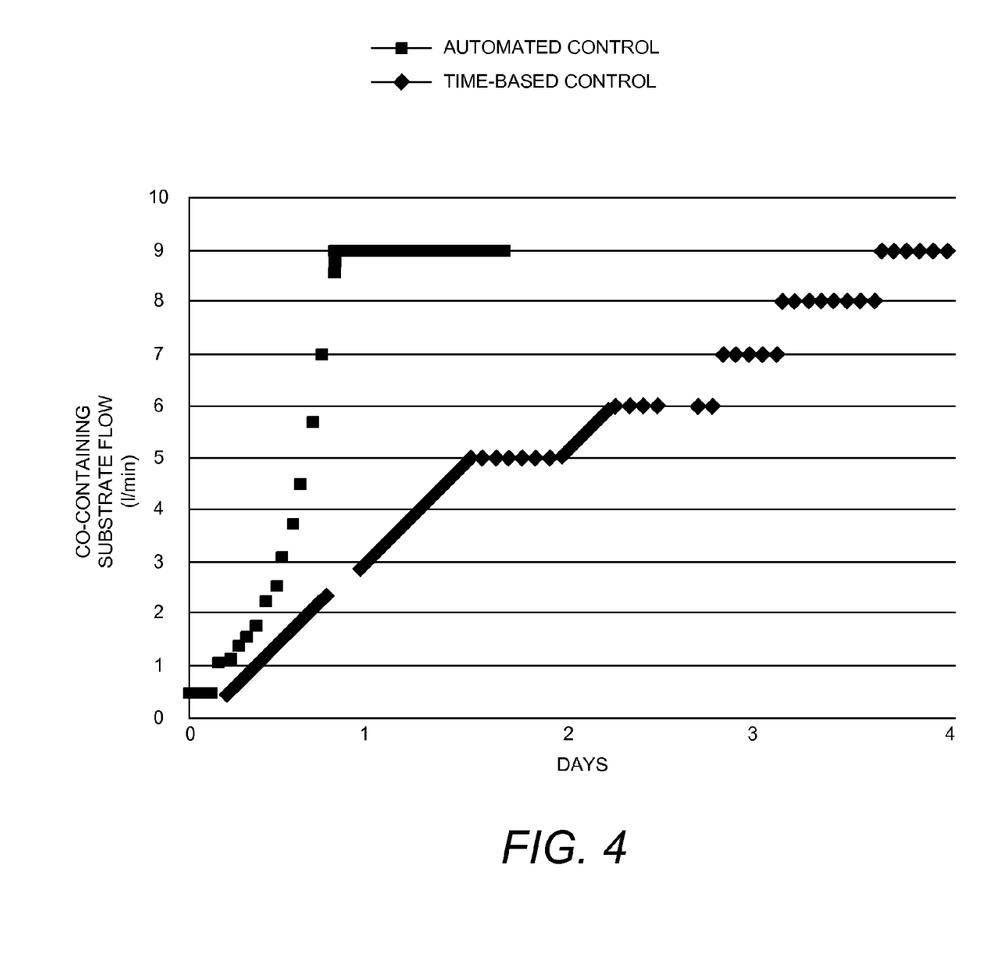
FIG. 4 is a comparative graph of the CO-containing substrate flow rate over time, for biological processes for converting a CO-containing substrate to ethanol, using a conventional control methodology and a control methodology as described herein.
Figure 5:
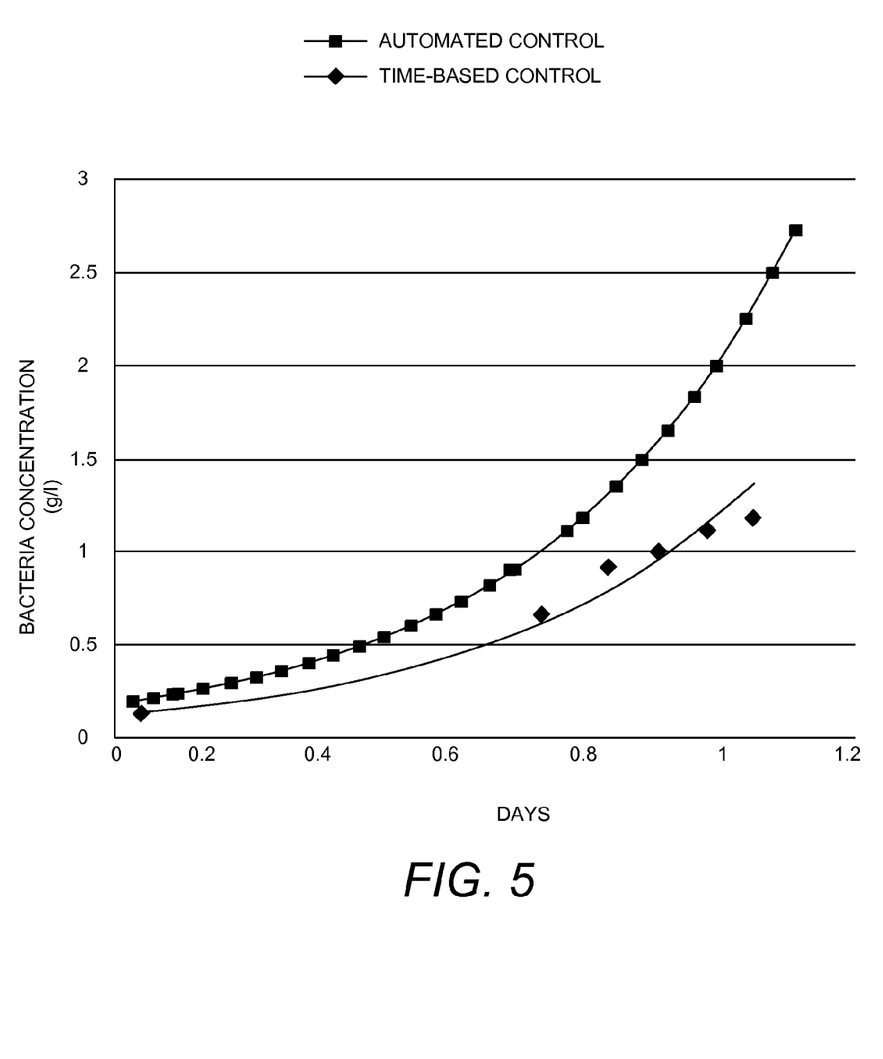
FIG. 5 is a comparative graph of the carboxydotrophic bacteria concentration in a culture medium over time, for biological processes for converting a CO-containing substrate to ethanol, using a conventional control methodology and a control methodology as described herein.

As is apparent from a comparison of FIGS. 2 and 3, the concentration of the desired product, ethanol, is less than 2 grams/liter (g/l) at Day 1 of the time-based startup, whereas this concentration is already nearly 8 g/l at this point in the automated startup. In addition, as illustrated in FIG. 4, it is apparent that the automated startup leads to an increase in the CO-containing substrate flow rate that is much faster, compared to the time-based start-up. This is due to the continual supply of the needed amount of CO to the bacterial culture for ethanol production, without oversupply that is detrimental to bacterial growth. In the case of the time-based profile, the flow rate of the CO-containing substrate was characteristically conservative, in order to ensure CO oversupply is avoided. As a result, however, CO undersupply is inevitable, and acetic acid is main product, rather than ethanol. FIG. 5 compares the concentrations of bacteria over time, for these start-up processes, using these two control methodologies. As is apparent, even with the higher CO flow rate in the case of the automated start-up, microbial growth is not inhibited, and in fact it is enhanced.

Based on these results, control methodologies as described herein can provide significant process benefits, particularly in terms of reducing the time needed to achieve a given process objective, such as a desired acetic acid concentration or bacteria concentration. The objective may be associated with the completion of an initial startup period, such as a batch operation period, in which case the transition to continuous operation may be attained more quickly and efficiently. This leads to important commercial benefits, including a reduced consumption of materials and reduced overall operating costs. In the case of a process operating with two reactors equipped with a cell recycle system, it may be possible to directly sample cell-free permeate from the reactors and feed these samples to an automated HPLC without any further treatment, i.e., without sample filtration or centrifugation. In contrast, conventional sample preparation methods, prior to injection to an HPLC, require the addition of specific acids or bases, followed by centrifugation or filtration. This involves manual pipetting, which adds complexity and results in greater error in the results.

Example 2

Automated Startup—Control of $NH_4OH$ Flow Based on Measured Concentrations

A biological process for the conversion CO to ethanol was started by inoculating a bioreactor with culture medium containing *C. ljundahlii*. The pH of culture medium began to drop as acetic acid was produced. CO-containing substrate and ammonium hydroxide feeds to the bioreactor were started when the pH of the culture medium reached 5.0. Based on the measured bacteria concentration in the bioreactor, an acetate (acetic acid) target concentration and a diluent flow rate were determined according to the following equations:

Acetate target concentration=$A_1 \cdot BIOCONmv + B_1$

Figure 6:
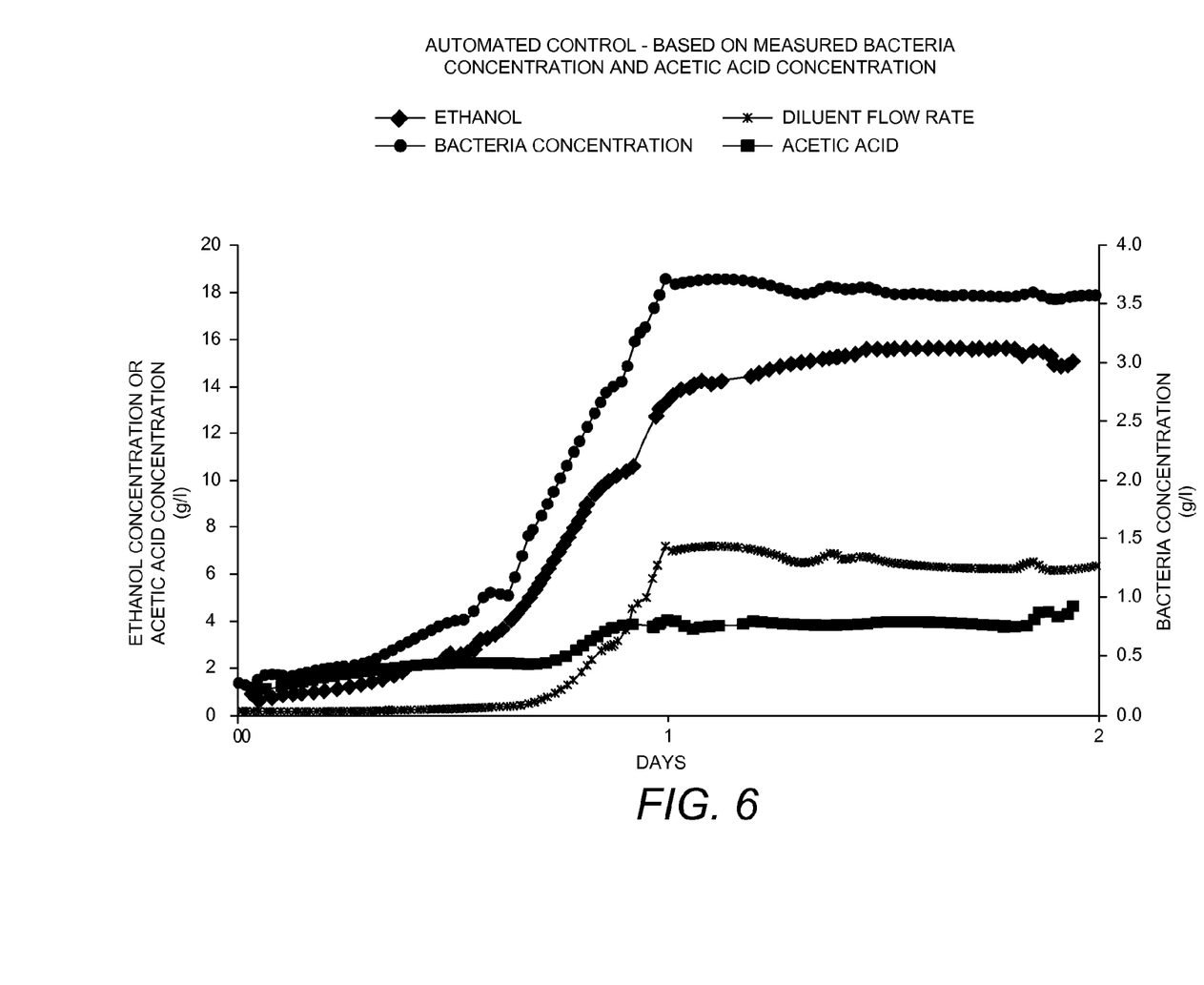
FIG. 6 is a graph of measured concentrations of ethanol, carboxydotrophic bacteria, and acetic acid, in a culture medium over time, as well as the measured flow rate of fresh culture medium, for a biological process for converting a CO-containing substrate to ethanol, using a representative control methodology as described herein.

Diluent flow rate=$C_1^{(BIOCONmv)}$

Wherein $A_1$, $B_1$, and $C_1$ were determined empirically from information obtained in prior processes. Based on the acetic acid concentration measured using the on-line HPLC, the flow rate of ammonium hydroxide was adjusted automatically, i.e., increased in order to increase the acetic acid production by the bacteria or decreased in order to decrease the acetic acid production. The flow of the gaseous CO-containing substrate was increased or decreased automatically in order to maintain the pH of the culture medium at target pH=5.0. The concentrations of ethanol, bacteria, and acetic acid over time, in addition to the flow rate of the diluent, are shown in FIG. 6.

Example 3

Automated Startup—Based on Measured pH and CO-Containing Substrate Flow Only

Based on previous start-up data for biological processes, as described in Example 1, in which CO was converted to ethanol by feeding it to a culture medium containing *C. ljundahlii*, relationships were established between a given bacterial concentration in the reactor, a corresponding flow rate of the CO-containing substrate of a given composition required that to yield a target acetic acid productivity, and a required ammonium hydroxide flow rate needed to maintain the culture medium pH at a given target. These relationships were as follows:

$W \cdot BIOPROD + X \cdot METPROD = NEUTFLO = Y \cdot COFLO + Z$ wherein BIOPROD, METPROD, NEUTFLO, and COFLO represented, respectively, the bacteria (biomass) productivity, the acetic acid (acetate) productivity, the $NH_4OH$ flow rate to the bioreactor, and the CO-containing substrate flow rate to the bioreactor. The factors W, X, Y and Z were determined empirically (using linear regression) from information obtained in prior processes, in which bacteria productivity measurements were based on concentrations measured at successive time intervals. That is, the measured bacterial productivity was calculated as bacteria concentration at Time 2−bacteria concentration at Time 1)/(Time 2−Time 1). In these prior processes, the bacteria concentration was measured using a spectrophotometer or plate reader or biomass probe, and the measured acetic acid productivity was calculated as acetic acid concentration at Time 2−acetic acid concentration at Time 1)/(Time 2−Time 1). Acetic acid and ethanol concentrations were measured by HPLC. According to the data generated from these prior processes, the following factors were determined: W=1.2, X=1.5, Y=1.46, and Z=3.21.

Thus, the relationship used for the automated startup was NEUTFLO=1.46·COFLO+3.21. The pH of the culture medium was maintained at 5.0 by adjusting the flow of the CO-containing substrate automatically using a PID controller. The relationships above were used to set the ammonium hydroxide flow rate, based on the measured flow rate of the CO-containing substrate.

Figure 7:
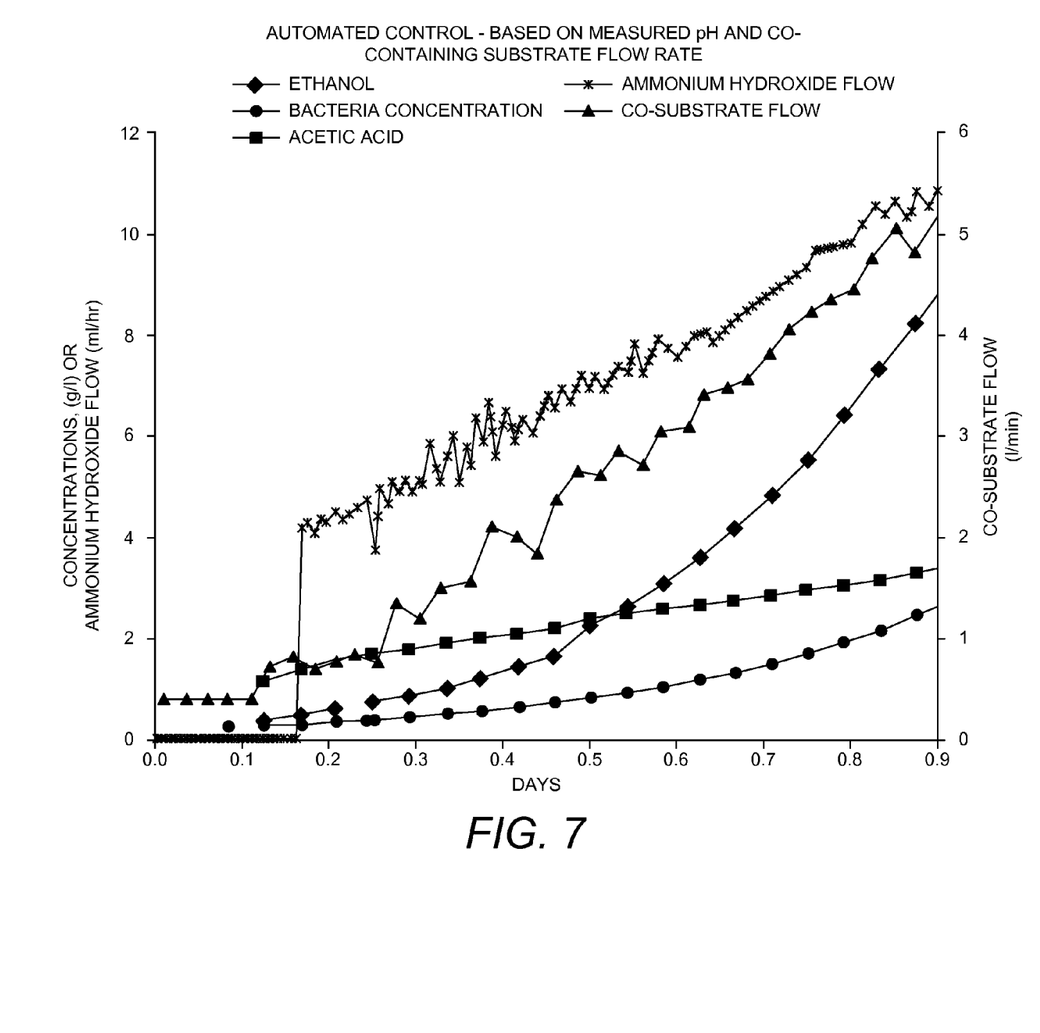
FIG. 7 is a graph of measured concentrations of ethanol, carboxydotrophic bacteria, and acetic acid in a culture medium over time, as well as the measured flow rates of $NH_4OH$ neutralizing agent solution and CO-containing substrate, for a biological process for converting a CO-containing substrate to ethanol, using an alternative control methodology as described herein.

The concentrations of ethanol, bacteria, and acetic acid over time, in addition to the flow rates of the ammonium hydroxide and CO-containing substrate, are shown in FIG. 7. Advantageously, the bacterial growth over the first day was high, at about 2.9 grams/(liter·day), and acetic acid productivity was low, at about 2.8 grams/(liter·day). Ethanol productivity and concentration were maximized. These observations were consistent with a successful startup of the biological CO conversion process, which is critical prior to establishing a continuous process. Importantly, the measured concentrations of bacteria and acetic acid in the bioreactor were not used directly in this control methodology. Rather, these concentrations were monitored, only to the extent to confirm progress of the operation, but without feedback into the automation.

Overall, aspects of the invention are directed to control methodologies for biological fermentation processes in which a CO-containing substrate is used to produce higher value products such as ethanol. The control methodologies may advantageously shorten the initiation or startup of these processes, such that continuous production is attained (e.g., upon reaching a given process initiation target) in a shorter time period after inoculation of the bioreactor, compared to time periods required using conventional control methodologies (e.g., a time-based profile for the flow of CO-containing substrate). These control methodologies may alternatively, or in addition, improve the productivities of the desired end product and/or improve the growth rate of the bacteria, during the initiation or startup. Those having skill in the art, with the knowledge gained from the present disclosure, will recognize that various changes can be made in control methodologies, systems, and computer program products, without departing from the scope of the present invention.

The invention claimed is:
1. A fermentation process comprising:
 a) feeding a gaseous substrate stream comprising CO and a basic neutralizing agent to a bioreactor comprising a carboxydotrophic bacterial culture in a liquid nutrient medium;
 b) fermenting the culture wherein at least a portion of the CO in the gaseous substrate stream is converted to a product comprising ethanol and an acidic metabolite;
 c) optimizing the production of said product by:
  1) measuring an acidic metabolite concentration, a carboxydotrophic bacteria concentration, and a carboxydotrophic bacteria productivity;
  2) determining an acidic metabolite set point concentration according to either formula (1) or (2):

$A1 \cdot BIOCONmv + B1$       (1)

$A2 \cdot BIOPRODmv + B2$       (2)

wherein BIOCONmv represents the carboxydotrophic bacteria measured concentration in the culture medium, BIOPRODmv represents the carboxydotrophic bacteria measured productivity and A1, A2, B1 and B2 are constants;

3) increasing a basic neutralizing agent flow rate if the acidic metabolite concentration is less than the acidic metabolite set point concentration; and 4) decreasing the basic neutralizing agent flow rate if the acidic metabolite concentration is greater than the acidic metabolite set point concentration.

2. The process of claim 1, wherein the acidic metabolite measured concentration is determined intermittently or continuously.

3. The process of claim 1, wherein the constants $A_1$, $A_2$, $B_1$, and $B_2$ are determined empirically from experimental data.

4. The process of claim 1, wherein the carboxydotrophic bacteria concentration is determined intermittently or continuously.

5. The process of claim 1, wherein the process is performed during a batch operation period.

6. The process of claim 1, wherein the CO-containing substrate is obtained from an industrial process selected from the group consisting of a steel manufacturing process, a non-ferrous product manufacturing process, a petroleum refining process, a biofuel production process, a coal gasification process, an electric power production process, a carbon black production process, an ammonia production process, a methanol production process, gasification of organic matter, steam reforming of hydrocarbons and a coke manufacturing process.

7. The process of claim 1, wherein the acidic metabolite is acetic acid.

8. The process of claim 1, wherein the basic neutralizing agent is ammonium hydroxide solution.

9. The process of claim 1, further comprising flowing a diluent to the bioreactor at a diluent flow rate which is determined by formulas (3) or (4)

$$C_1^{(BIOCONmv)} \quad (3)$$

$$C_2^{(BIOPRODmv)} \quad (4)$$

wherein BIOCONmv represents the carboxydotrophic bacteria concentration in the culture medium, BIOPRODmv represents the carboxydotrophic bacteria measured productivity and $C_1$ $C_2$ are constants determined empirically from experimental data.

10. A fermentation process comprising;
a) feeding a substrate stream comprising CO and a basic neutralizing agent to a bioreactor comprising a carboxydotrophic bacterial culture in a liquid nutrient medium;
b) fermenting the culture wherein at least a portion of the CO in the gaseous substrate stream is converted to a product comprising ethanol and an acidic metabolite;
c) optimizing the production of said product by adjusting a basic neutralizing agent flow rate to the bioreactor, the basic neutralizing agent flow rate determined by a formula:

$$Y \cdot COFLOmv + Z \quad (1)$$

wherein COFLOmv represents a substrate stream flow rate, and Y and Z are constants determined empirically from experimental data.

* * * * *